United States Patent [19]
Warner et al.

[11] Patent Number: 6,084,128
[45] Date of Patent: Jul. 4, 2000

[54] SULFUR REMOVAL PROCESS FROM AN ACRYLATE STREAM

[75] Inventors: R. Jay Warner, Corpus Christi; Martiniano Garza, Jr., Houston; Hermelinda Pedraza; Carolyn Supplee, both of Corpus Christi, all of Tex.

[73] Assignee: Celanese International Corporation, Dallas, Tex.

[21] Appl. No.: 09/438,110

[22] Filed: Nov. 10, 1999

Related U.S. Application Data

[63] Continuation of application No. 08/962,426, Oct. 31, 1997, abandoned.

[51] Int. Cl.$^7$ .................................................. C07C 51/42
[52] U.S. Cl. .............................................................. 562/600
[58] Field of Search ............................................... 562/600

[56] References Cited

U.S. PATENT DOCUMENTS

| | | |
|---|---|---|
| 3,450,749 | 6/1969 | Furrow . |
| 3,888,917 | 6/1975 | Fentress et al. . |
| 4,212,821 | 7/1980 | Marquis et al. . |
| 4,450,047 | 5/1984 | Malzahn . |
| 4,885,383 | 12/1989 | Weber et al. . |
| 5,075,416 | 12/1991 | Staeglich et al. . |
| 5,386,052 | 1/1995 | Sakakura . |
| 5,434,279 | 7/1995 | Wimmer . |
| 5,928,980 | 7/1999 | Gangwal . |

FOREIGN PATENT DOCUMENTS

| | | |
|---|---|---|
| 0 331 864 A1 | 1/1989 | European Pat. Off. . |
| 382454 | 8/1990 | European Pat. Off. . |
| 0 736 523 A2 | 3/1996 | European Pat. Off. . |
| 706813 | 4/1996 | European Pat. Off. . |
| 018789 | 9/1972 | Japan . |
| 50-115689 | 9/1975 | Japan . |
| 54-009219 | 1/1979 | Japan . |
| 6234699 | 2/1993 | Japan . |
| 06234700 | 8/1994 | Japan . |
| 9923059 | 5/1999 | WIPO . |

*Primary Examiner*—Paul J. Killos
*Attorney, Agent, or Firm*—M. Susan Spiering

[57] ABSTRACT

Broadly, the present invention is directed to a process for the removal of sulfur from an acrylate stream. In particular, disclosed is a process for the recovery and reuse of an acid catalyst employed primarily in the reaction to form acrylic esters. Reaction end components which include the acid catalyst employed in the reaction process, are directed to an extractor for contact with water. Upon contact with water, a phase separation occurs between the acid catalyst/water mixture and other organic matter. The organic matter is sent forward for product purification while the acid/water mixture is recycled to the reaction process.

The present invention employs the use of an extractor to aid in the separation of the acid catalyst from the reaction by-products. This removal of acid results in fewer organic sulfur components to be emitted from the reaction process and hence is a more environmentally friendly process.

4 Claims, No Drawings

SULFUR REMOVAL PROCESS FROM AN ACRYLATE STREAM

This application is a continuation of U.S. Ser. No. 08/962,426 filed Oct. 31, 1997 now abandoned.

FIELD OF THE INVENTION

This invention relates to an improved process for producing acrylic esters. More particularly, this invention provides a method for removal of sulfur from an acrylate stream. The sulfur is typically in the form of an alkane sulfonic acid compound, and is generally used as an acid catalyst for the esterification reaction. This acid catalyst may be efficiently recovered, recycled, and reused via the disclosed process.

BACKGROUND OF INVENTION

Esterification reactions for the production of acrylic esters are well known in the art. The esterification generally involves the reaction of an (meth)acrylic acid and alcohol having 4 or more carbon atoms, in the presence of a strong acid catalyst to produce the corresponding desired ester. U.S. Pat. No. 5,386,052, herein incorporated by reference in its entirety, describes the reaction generally, and claims a process for producing acrylic or methacrylic esters. Examples of acids employed in the reaction process include, but are not limited to sulfuric acid, p-toluenesulfonic acid, benzenesulfonic acid, xylenesulfonic acid, naphthenesulfonic acid, methanesulfonic acid, ethanesulfonic acid, and the like. These strong acids must be removed from the reaction liquid after the reaction is completed. The acid then must be disposed. Currently, all methods of disposal have an environmental impact. One method is to dilute the acid with water. Thereafter the water must be treated and disposed. Accordingly, the acid must also be separated from the water and disposed, usually by incineration, or recovered.

U.S. '052 also describes a method for the removal of the acid whereby the reaction liquid (containing a predominantly desired ester product which is water insoluble) is extracted with water, separated from the aqueous solution containing the acid catalyst, and recycling the aqueous solution.

Also described in U.S. '052 is a method for removing the strong acid in which the reaction liquid is treated with an aqueous alkaline solution for neutralization (Japanese Laid-Open Patent Publications Nos. 243046/1986, 34965/1991 and 230240/1992). According to this method, a large amount of alkali is needed for effecting a sufficient neutralization. Moreover, it is very difficult to separate and recover the acid catalyst and unreacted acrylic or methacrylic acid from the aqueous alkaline solution after the treatment and, therefore, the aqueous alkaline solution must be disposed as a waste after the treatment. A drawback of this method is the production of a large amount of waste water which contains a high concentration of potentially harmful organic acid salts.

Due to the above drawbacks, it is desirable to remove as much sulfur containing compounds from process steams as possible, so as to minimize environmental impact(s). It is also desirable to recover and reuse the acid catalyst so as to reduce the overall costs involved in the esterification reaction, as well as reduce the labor and expense involved in any acid disposal.

SUMMARY OF THE INVENTION

In the esterification reaction to produce 2-ethylhexylacrylate (2-EHAcA), acrylic acid (AA) and 2-ethylhexanol (2-EHOH) are reacted in the presence of a catalyst; generally methanesulfonic acid (MSA) and solvent such as cyclohexane, toluene, benzene and the like. These solvents form a low boiling azeotrope with the water formed during the esterification reaction. MSA may be recovered by a water extraction process during the course of the esterification reaction. The MSA phases out of the reaction and may be extracted by the water of reaction formed in-situ.

The reaction product stream is allowed to contact and mix with water. The mixture is then directed into a decanter for phase separation. A separable phase is formed between the water/MSA phase and the organic stream from the acrylate reaction process. The MSA/water phase is then recycled to the esterification reaction process. The recovery process may also employ other mechanic equipment such as a continuous stirred tank reactor (CSTR) or an static in-line mixer (SILM) to achieve the organic/water mixture. Although this process is discussed in terms of recovery of MSA and the reaction to form 2-EH acrylate, it can also be employed for the recovery of other acids, particularly other sulfuiric acids in the reaction to form other (homolog) esters.

In one aspect, the present invention is directed to a process for the removal of sulfur from an acrylate reaction product stream comprising:

(a) contacting in a reactor (meth)acrylic acid with an alcohol in the presence of a sulfonic acid catalyst and solvent to form a reaction mixture containing the corresponding ester reaction product, water, solvent, and residue byproducts;

(b) directing the reaction mixture to a decanter and allowing the reaction mixture of (a) sufficient time to form a two phase system comprising as phase (1) acid catalyst/water, and as phase (2) reaction product, acrylic ester, solvent, heavy ends, and oligomers; and, (c) recycling phase (1) of (b) containing acid catalyst to the reactor of (a).

The present invention may employ the use of an extractor in place of a decanter to aid in the separation of the acid catalyst from the reaction by-products. The removal of acid (which contains sulfur) results in fewer organic sulfur components to be emitted from the reaction process and hence is a more environmentally friendly process. Accordingly, the acid catalyst used for the esterification reaction and unreacted (meth)acrylic acid can be effectively recovered and reused for the reaction. The amount of catalyst to be used in the reaction process can be considerably reduced. This process eliminates the need for a treatment of the reaction liquid with an alkali, per the art, meaning that the production of a large amount of waste water containing harmful organic salt(s) can be avoided.

DETAILED DESCRIPTION OF THE INVENTION

The present process involves separation and recovery of mixtures of MSA, 2-EH acrylate, solvent, and acrylic acid (AA) by liquid-liquid extraction or decantation using water. The reaction stream, is obtained from a 2-EH acrylate manufacturing processing involving the use of a liquid sulfonic acid catalyst (e.g., MSA) for the reaction of 2-ethylhexanol and acrylic acid in a solvent.

In one aspect, the present invention is directed to a process for the removal of sulfur from an acrylate reaction product stream comprising:

(a) contacting in a reactor (meth)acrylic acid with an alcohol and solvent in the presence of a sulfuric acid catalyst and an aqueous environment to form a reaction mixture containing the corresponding ester reaction product and residue byproducts;

(b) removing the reaction product from the reaction mixture;

(c) contacting the reaction mixture of (b) in a decanter with water to form a two phase system comprising as phase (1) acid catalyst/water, and as phase (2) reaction product, acrylic ester, solvent, heavy ends, and oligomers; and, (d) recycling phase (1) of (c) containing acid catalyst to the reactor of (a).

Alternatively, the present invention is directed to a process for the recovery of acid catalyst employed during the production of an acrylic ester comprising the steps noted above.

In an aspect of the inventive reaction process, an alcohol, preferably having 4 or more carbon atoms is reacted with an (meth)acrylic acid in the presence of an acid catalyst to form an acrylate ester; said acid catalyst containing at least one sulfur moiety. In the present invention, any alcohol selected from aliphatic, alicyclic and aromatic alcohols can be used as the alcohol. Examples of the aliphatic alcohols include but are not limited to butyl alcohol, pentyl alcohol, hexyl alcohol, heptyl alcohol, octyl alcohol, 2-ethylhexyl alcohol, nonyl alcohol, decyl alcohol, dodecyl alcohol, hexadecyl alcohol and stearlyl alcohol. Examples of the alicyclic alcohols include cyclopentyl alcohol, cyclohexyl alcohol, ethylcyclohexyl alcohol, ethylcyclohexyl alcohol and butylcyclohexyl alcohol. Examples of the aromatic alcohols include benzyl alcohol, methylbenzyl alcohol, dimethylbenzyl alcohol and butylbenzyl alcohol. Examples of polyols which may be employed include trimethyololpropane, pentaerythritol, hexanediol, ethyleneglycol, 1,3- or 1,4-butanediol, and the like.

Exemplary solvents to employ in the esterification include: toluene, benzene, xylene, cyclohexane, and the like.

As the acid catalyst for esterification, toluenesulfonic acid, benzenesulfonic acid, xylenesulfonic acid, ethanesulfonic acid, triflorosulfonic acid, and methanesulfonic acid may be employed. Methanesulfonic acid is preferred. Sulfuric acid has frequently been used as a catalyst for esterification. Sulfuric acid is not recommended since it may be difficult to efficiently remove from the esterification reaction and due to its corrosive nature.

In the esterification reaction between acrylic or methacrylic acid (herein referred to as (meth)acrylic acid) and an alcohol, the starting (meth)acrylic acid and the alcohol are usually supplied to the reaction in the general molar ratio range of about 1.0:1.2–1.0:0.8. The amount of the acid catalyst used is generally from about 0.1 to 5.0% by weight, preferably from about 0.5 to 2.0% by weight of the reactants. The reaction is carried out generally at a temperature of about 100° C. while reaction water produced in the course of esterification is preferably removed by azeotropic distillation. In order to facilitate the removal of reaction water, an inert azeotropic agent may be used. Hydrocarbons such as benzene, toluene, xylene, and cyclohexane are commonly used as the azeotropic agent. The removal of reaction water may also be conducted by conventional means such as membrane separation using a vapor separation membrane, or by a method other than distillation. In order to prevent the loss of (meth)acrylic acid or the ester due to the occurrence of unfavorable polymerization thereof, a polymerization inhibitor or an oxygen-containing gas is usually added to the reactor. Common polymerization inhibitors include phenothiazine (PTZ), hydroquinone (HQ), methyl ester of hydroquinone (MEHQ) and the like.

A reactor product stream containing unreacted alcohol, solvent, and (meth)acrylic acid, the corresponding ester, the acid catalyst, heavy end oligomers, and a trace amount of any polymerization inhibitor employed is directed to an extractor wherein water (contained-that water produced in-situ- or otherwise) is added to phase separate the sulfonic acid from other components present in the reaction product. Water is to be present in a minimal amount, or that amount necessary to phase separate the catalyst from the reaction product. The more water present in the reaction means that a greater load is placed on the reaction system to subsequently remove the water. If necessary, water may be added at about a 1:1 molar ratio of water to organic feed. The organic feed stream temperature is generally less than about 100° C. The recycled process water added for phase separation is generally at a temperature of about 70° C. or lower. Mixer rates are variable based on the composition of the mixture to separate, the type of acid employed, the temperatures employed within the extractor, etc. Mixer rates within the extractor should be sufficient to allow mass transfer needed for efficient extractions.

Mechanical devices which can employed for this extraction process, include static in-line mixer (SILM) which functions similar to an extraction column. It is important to the extraction process that a good mass transfer is achieved between the water/organic phase.

Although fresh water can be used in the extractor/decanter, the reaction water (i.e., overhead water from reactor column) produced in the esterification reaction and removed from the reaction system may also be employed in the extractor/decanter column for recovery of the sulfonic acid catalyst. The use or recycling of reaction water has the advantage that the amount of waste water in the system can be reduced.

After contact, the water phase containing MSA is taken from the bottom of the extractor/decanter and directed back to the reactor for reuse as a catalyst. Greater than 50% MSA may be recovered under the present inventive process. The MSA has been shown to be active and reusable for continued esterification reactions.

It will be understood by those of skill in the art that the present invention, although explained in relation to 2-EH acrylate and MSA, the process is also applicable to production of multi functional monomers (MFM's) and MSA as catalyst for their production. MFM's is broadly defined as the reaction product of a (meth)acrylate and a polyol. Examples of MFM's include trimethylol triacrylate, hexane diol diacrylate, tetra ethylene glycol diacrylate, and the like.

What is claimed is:

1. A process for the removal of sulfur from an acrylate reaction product stream comprising:

(a) contacting in a reactor (meth)acrylic acid with an alcohol in the presence of a sulfonic acid catalyst and solvent to form a reaction mixture containing the corresponding ester reaction product, water, solvent, and residue byproducts;

(b) directing the reaction mixture to a decanter and allowing the reaction mixture of (a) sufficient time to form a two phase system comprising as phase (1) acid catalyst/water, and as phase (2) reaction product, acrylic ester, solvent, heavy ends, and oligomers; and, (c) recycling phase (1) of (b) containing acid catalyst to the reactor of (a).

2. The process according to claim 1, wherein the acid catalyst is selected from the group consisting of methanesulfonic acid, benzenesulfonic acid, toluenesulfonic acid and xylenesulfonic acid.

3. The process according to claim 2, wherein the acid is methanesulfonic acid.

4. The process of claim 1 wherein water is added to the reaction mixture to enhance phasing.

* * * * *